US009681833B2

(12) United States Patent
Olsavsky et al.

(10) Patent No.: US 9,681,833 B2
(45) Date of Patent: Jun. 20, 2017

(54) COEXTRUDED PLASTIC CAPILLARY TUBE (71) Applicant: Tekni-Plex, Inc., King of Prussia, PA (US)

(72) Inventors: Joseph E. Olsavsky, Waterville, OH (US); Steve Schlater, Toledo, OH (US)

(73) Assignee: Tekni-Plex, Inc., Wayne, PA (US)

( * ) Notice: Subject to any disclaimer, the term of this patent is extended or adjusted under 35 U.S.C. 154(b) by 656 days.

(21) Appl. No.: 14/256,342

(22) Filed: Apr. 18, 2014

(65) Prior Publication Data

US 2015/0298128 A1 Oct. 22, 2015

(51) Int. Cl.
*A61B 5/15* (2006.01)
*B29C 47/06* (2006.01)
(Continued)

(52) U.S. Cl.
CPC .......... *A61B 5/150007* (2013.01); *A61B 5/15* (2013.01); *A61B 5/15003* (2013.01); *A61B 5/150022* (2013.01); *A61B 5/150038* (2013.01); *A61B 5/150045* (2013.01); *A61B 5/150206* (2013.01); *A61B 5/150274* (2013.01); *A61B 5/150343* (2013.01); *B01L 3/502* (2013.01); *B01L 3/502707* (2013.01); *B01L 3/561* (2013.01); *B29C 47/0023* (2013.01); *B29C 47/0026* (2013.01); *B32B 1/08* (2013.01); *B32B 27/08* (2013.01); *B32B 27/285* (2013.01);
(Continued)

(58) Field of Classification Search
CPC . A61B 5/15; A61B 5/150022; A61B 5/15003; A61B 5/150038; A61B 5/150045; A61B 5/150274; A61B 5/150142; A61B 5/150007; A61B 5/150206; A61M 25/00; A61M 25/0009; A61M 25/0021; A61M 25/0043; A61M 25/0067; B29C 47/0023; B29C 47/006; B29C 47/0065; Y10T 428/1393
See application file for complete search history.

(56) References Cited

U.S. PATENT DOCUMENTS 5,059,398 A 10/1991 Kenney
5,318,525 A * 6/1994 West ................. A61B 18/1492
600/585
(Continued)

FOREIGN PATENT DOCUMENTS

EP 2154402 2/2010
JP H06277289 10/1994
(Continued)

OTHER PUBLICATIONS

Int'l. Preliminary Report on Patentability mailed May 4, 2016 in corresponding Int'l. Appln. No. PCT/US2015/025701.
(Continued)

Primary Examiner — Walter B Aughenbaugh
(74) Attorney, Agent, or Firm — Polsinelli PC (57) ABSTRACT

Coextruded plastic capillary tube and method of manufacturing a coextruded tube for collecting a volume of liquid. The tube is disposable, inexpensive to manufacture and can reliably draw blood and other aqueous based fluids into the tube by capillary action, at a fluid uptake level comparable to glass and other commercially pre-treated plastic tubes, without requiring further interior coating.

28 Claims, 5 Drawing Sheets

(51) Int. Cl.

| | | |
|---|---|---|
| *B01L 3/00* | (2006.01) | |
| *F16L 11/00* | (2006.01) | |
| *G01N 1/14* | (2006.01) | |
| *B32B 27/34* | (2006.01) | |
| *B32B 27/36* | (2006.01) | |
| *B32B 1/08* | (2006.01) | |
| *B32B 27/08* | (2006.01) | |
| *B32B 27/28* | (2006.01) | |
| *B32B 27/30* | (2006.01) | |
| *B32B 27/32* | (2006.01) | |
| *F16L 11/04* | (2006.01) | |
| *B29C 47/00* | (2006.01) | |
| *B29K 71/00* | (2006.01) | |
| *B29K 77/00* | (2006.01) | |
| *B29K 96/04* | (2006.01) | |
| *B29K 105/00* | (2006.01) | |
| *B29L 9/00* | (2006.01) | |
| *B29L 23/00* | (2006.01) | |
| *G01N 1/02* | (2006.01) | |

(52) U.S. Cl.
CPC .......... *B32B 27/302* (2013.01); *B32B 27/308* (2013.01); *B32B 27/32* (2013.01); *B32B 27/34* (2013.01); *B32B 27/36* (2013.01); *F16L 11/00* (2013.01); *F16L 11/04* (2013.01); *G01N 1/14* (2013.01); *B01L 2200/085* (2013.01); *B01L 2300/0838* (2013.01); *B01L 2300/0858* (2013.01); *B01L 2300/0887* (2013.01); *B01L 2300/165* (2013.01); *B01L 2400/0406* (2013.01); *B29C 47/0004* (2013.01); *B29C 47/065* (2013.01); *B29K 2071/00* (2013.01); *B29K 2077/00* (2013.01); *B29K 2096/04* (2013.01); *B29K 2105/0085* (2013.01); *B29K 2995/004* (2013.01); *B29K 2995/0097* (2013.01); *B29L 2009/00* (2013.01); *B29L 2023/007* (2013.01); *B32B 2250/24* (2013.01); *B32B 2270/00* (2013.01); *B32B 2307/546* (2013.01); *B32B 2535/00* (2013.01); *B32B 2597/00* (2013.01); *G01N 2001/028* (2013.01); *G01N 2001/149* (2013.01); *Y10T 428/1393* (2015.01)

(56) References Cited

U.S. PATENT DOCUMENTS

| | | | |
|---|---|---|---|
| 5,429,605 A * | 7/1995 | Richling | A61M 25/1006 604/103.11 |
| 5,460,782 A | 10/1995 | Coleman et al. | |
| 5,618,272 A | 4/1997 | Nomura | |
| 5,947,940 A * | 9/1999 | Beisel | A61M 25/005 604/264 |
| 6,531,098 B1 | 3/2003 | Kenney | |
| 7,674,411 B2 | 3/2010 | Berg et al. | |
| 8,070,719 B2 | 12/2011 | Lee et al. | |
| 2003/0018320 A1 | 1/2003 | Scheu | |
| 2004/0241364 A1* | 12/2004 | Zihlmann | B29C 45/16 428/35.7 |
| 2007/0128589 A1* | 6/2007 | Sanders | C07K 7/06 435/5 |
| 2008/0154239 A1 | 6/2008 | Gielenz et al. | |
| 2008/0188832 A1* | 8/2008 | Tanioka | A61B 8/445 604/525 |
| 2008/0293999 A1 | 11/2008 | Halahmi | |
| 2009/0259183 A1 | 10/2009 | Chong et al. | |
| 2010/0049192 A1 | 2/2010 | Holtz et al. | |

FOREIGN PATENT DOCUMENTS

| | | |
|---|---|---|
| JP | 2004008628 | 1/2004 |
| WO | 9741906 A1 | 11/1997 |
| WO | 2006123975 A1 | 11/2006 |
| WO | 2009135098 A1 | 11/2009 |

OTHER PUBLICATIONS

PEBAX® MV 1074 SA 01 MED, Arkema Specialty Polyamides, Arkema Innovative Chemistry, Columbes Cedex, France, http://www.pebax.com/en/applications, Web. Feb. 10, 2014.

PEBAX® MED Polyether Block Amide, Foster Custom Compounds, Putnam, CT, http://www.fosterpolymers.com/polymers/prebax.php, Web. Apr. 21, 2014.

First Office Action dated Mar. 3, 2017 in corresponding Chinese application CN 201580008094.X (In the first Office Action, the Examiner's objections are raised as directed to the added metric units in the claims. Since the Examiner merely objects to some literal deficiencies without commenting on the merits of the invention, an English translation of the Office Action seems unnecessary.).

* cited by examiner

Table 1

| Comparison Sample | Description | Sidewall Thickness (T) (Inch) | Capillary Action (Inch) |
|---|---|---|---|
| 1 | Monolayer Tube - Eastman PETG 6763 | 0.014 | 0.09 |
| 2 | Monolayer Tube - DAK Laser + C 9921 PET | 0.014 | 0.09 |
| 3 | Pulmolab Soda Lime Glass Untreated (51602) | 0.007 | 1.68 |
| 4 | Pulmolab Soda Lime Glass Ammonium Heparin Internally Coated (51608) | 0.007 | 1.17 |
| 5 | Pulmolab Plastic - Ammonium Heparin Internally Coated (51684) | 0.014 | 1.31 |

FIG. 4

Table 2

| Example | Tube Description | Tube Construction Materials | Inner Wall Thickness (Layer 22) (Inch) | Intermediate Wall Thickness (Layer 23) (Inch) |
|---|---|---|---|---|
| 1 | 2M2L | Eastman PETG 6763 (Layer 24); 85% Eastman PETG 6763 + 15% Arkema Pebax MV1074 (Layer 22) | 0.002 | --- |
| 2 | 2M2L | Eastman PETG 6763 (Layer 24); 85% Eastman PETG 6763 + 15% Arkema Pebax MV2080 (Layer 22) | 0.002 | --- |
| 3 | 2M2L | Eastman PETG 6763 (Layer 24); Arkema Pebax MV1074 (Layer 22) | 0.005 | --- |
| 4 | 2M2L | Eastman PETG 6763 (Layer 24); 50% Arkema MV1074 + 50% Lyondell-Basell UE 672 EVA (Layer 22) | 0.002 | --- |
| 5 | 2M2L | Eastman PETG 6763 (Layer 24); Arkema Pebax 400 (Layer 22) | 0.002 | --- |
| 6 | 2M2L | Eastman PETG 6763 (Layer 24); 25% Eastman PETG 6763 + 75% Arkema Pebax 400 (Layer 22) | 0.002 | --- |
| 7 | 2M2L | Eastman PETG 6763 (Layer 24); 50% Eastman PETG 6763 + 50% Arkema Pebax 400 (Layer 22) | 0.002 | --- |
| 8 | 2M2L | Eastman PETG 6763 (Layer 24); Lyondell-Basell UE 672 EVA (Layer 22) | 0.002 | --- |
| 9 | 2M2L | DAK Laser +C 9921 PET (Layer 24); Arkema Pebax MV1074 (Layer 22) | 0.002 | --- |
| 10 | 3M3L | Eastman PETG 6763 (Layer 24); DAK Laser +C 9921 PET (Layer 23); Arkema Pebax MV1074 (Layer 22) | 0.002 | 0.008 |

| Outermost Wall Thickness (Layer 24) (Inch) | Sidewall Thickness (T) (Inch) | Capillary Action (Inch) |
| --- | --- | --- |
| 0.012 | 0.014 | 1.68 |
| 0.012 | 0.014 | 0.77 |
| 0.009 | 0.014 | 1.53 |
| 0.012 | 0.014 | 1.34 |
| 0.012 | 0.014 | 0.88 |
| 0.012 | 0.014 | 0.93 |
| 0.012 | 0.014 | 0.85 |
| 0.012 | 0.014 | 0.01 |
| 0.012 | 0.014 | 1.51 |
| 0.004 | 0.014 | 1.60 |

FIG. 5B

COEXTRUDED PLASTIC CAPILLARY TUBE

BACKGROUND

1. Technical Field

The present invention is in the field of liquid handling, and more specifically in the field of capillary tubes for collecting and transferring a volume of liquid such as blood from one point to another for testing or the like.

2. Introduction

Capillary tubes have long been used to collect and dispense fluids. They are commonly used in medical and research fields to extract very small (micro-liter) samples of liquids to be analyzed, such as blood samples for diabetics to determine glucose levels.

The simplest type of capillary tube is a glass or plastic tube open at both ends. For use in drawing blood, the patient's finger may be pricked with a lancet, allowing blood droplets to form at the incision point, and then one end of the capillary tube is placed adjacent to the incision site whereby blood is drawn into the tube via capillary action. The sample in the tube may then be transferred to another device, for testing or analysis. The inherent rigidity of a glass tube is quite desirable for handling by the phlebotomist and glass tubes are inexpensive to manufacture. However glass tubes are brittle, thus are prone to breakage and pose a safety concern should they break during packaging, distribution, transport or while in use.

Plastic capillary tubes are also commercially available. Plastic tubes are less likely to break than a glass tube due to the inherent toughness of some plastic materials in comparison to glass. However, depending on the polymer used to make the tube, they may not be as effective as glass at drawing blood into the tube. They may require pre-treating the interior of the tube so as to be rendered "wettable", so that the desired fluid can be drawn into the tube by capillary action. Many plastic tubes are pre-treated prior to use with an interior coating, such as an ammonium heparin coating, for this purpose, but the coating process can be labor, process and capital intensive and render the tubes less cost effective.

Thus there is an ongoing need for capillary tubes, particularly in medical applications, that can be manufactured on a cost effective basis that is competitive with glass tubes.

SUMMARY OF THE INVENTION

A coextruded plastic capillary tube and method of manufacture are provided in accordance with the present invention. The tube is disposable, inexpensive to manufacture and can reliably draw blood and other aqueous based fluids into the tube by capillary action, at a fluid uptake level comparable to glass and other commercially pre-treated plastic tubes, without requiring further coating.

In accordance with one embodiment of the invention, a coextruded multilayer capillary tube is provided comprising: a tubular sidewall defining a central channel and comprising at least two coextruded polymer layers coaxially disposed along an axial length of the tube between open proximal and distal ends of the tube; the tubular sidewall having an inner diameter sized to permit an aqueous or aqueous based fluid to flow into the central channel by capillary action through an open end of the tube; the at least two coaxial coextruded polymer layers comprising: an innermost layer defining the surface of the central channel comprising a polyether block polyamide (PEBA) polymer material; and an outer layer of a material having a flexural modulus of at least about 250,00 pounds per square inch (psi).

In one embodiment, the material comprising the innermost layer has a flexural modulus of at least about 11,000 psi.

In one embodiment, the innermost layer material comprises a blend of PEBA and a base resin.

In one embodiment, the base resin is selected from the group consisting of polyesters, acrylic resins, styrenic resins, acetal resins, polyamides, polyolefins and polyolefin copolymers, and all combinations and blends thereof.

In one embodiment, the central channel has a diameter in a range of from about 0.01 inches to about 0.10 inches; the tube wall has a thickness in a range of form about 0.003 inches to about 0.060 inches; and the innermost layer has a thickness in a range of from about 0.001 inches to about 0.059 inches.

In one embodiment, the tube wall has two layers, including an outer layer of semi-crystalline or amorphous polyester polymer material, and an innermost layer comprising PEBA or a blend of PEBA and a base resin.

In one embodiment, the tube wall has two layers and the central channel has a diameter in a range of from about 0.01 inches to about 0.10 inches; the tube wall has a thickness in a range of from about 0.003 inches to about 0.060 inches; and the innermost layer has a thickness in a range of from about 0.001 inches to about 0.059 inches.

In one embodiment, the tube wall has three layers, including an outermost layer comprising semi-crystalline or amorphous polyester polymer material, an intermediate layer comprising semi-crystalline or amorphous polyester polymer material, and an innermost layer comprising PEBA or a blend of PEBA and a base resin.

In one embodiment, the tube wall has three layers and the outermost layer has a thickness in a range of from about 0.0005 inches to about 0.058 inches, the intermediate layer has a thickness in a range of from about 0.0005 inches to about 0.058 inches, the innermost layer has a thickness in a range of from about 0.001 inches to about 0.059 inches, and the central channel has a diameter in a range of from about 0.01 inches to about 0.100 inches.

In one embodiment, the sidewall has an outermost layer of semi-crystalline polyester polymer material.

In one embodiment, the tube comprises a medical tube for collecting a sample of blood or other aqueous based fluid.

In one embodiment, a medical device is provided including the coextruded multilayer capillary tube for collecting a sample of blood or other aqueous based fluid.

In one embodiment, a method of collecting a fluid sample is provided comprising inserting an open end of the coextruded multilayer capillary tube into a fluid specimen and drawing fluid from the specimen into the channel via capillary action.

In one embodiment, the tube is sized for collecting a sample of at least 0.5 microliters.

In one embodiment, the tube is sized for collecting a sample of from about 0.5 to about 2 microliters.

In accordance with another embodiment of the invention, a method of making a coextruded multilayer capillary tube is provided comprising: coextruding a tubular sidewall of at least two coextruded polymer layers coaxially disposed along an axial length of the tube, the tubular sidewall defining a central channel for receiving a fluid, the tubular sidewall having an inner diameter sized to permit an aqueous or aqueous based fluid to flow into the central channel by capillary action through an open end of the tube, the at least two coaxial coextruded polymer layers comprising: an innermost layer defining the surface of the central channel comprising a polyether block polyamide (PEBA) polymer material, and an outermost layer of a material having a flexural modulus of at least about 250,000 pounds per square inch (psi).

Additional aspects and/or advantages of the invention will be set forth in the description which follows.

BRIEF DESCRIPTION OF THE DRAWINGS

These and/or other aspects and advantages of the invention will become apparent and more readily appreciated from the following description of various embodiments, taken in conjunction with the accompanying drawings of which.

DETAILED DESCRIPTION

Reference will now be made in detail to various embodiments of the present invention, examples of which are illustrated in the accompanying drawings, wherein like reference numerals refer to the like elements throughout.

FIGS. 1-3A illustrate a two layer capillary tube 1 according to one embodiment of the invention. The tube comprises an elongated tubular sidewall 2 surrounding a central axial tubular bore or channel 6, and is open at both ends 3, 4. The tube has an inner diameter ID for admitting a liquid into the tube by capillary action via an open distal end 3, and an open proximal end 4 for passing air from the tube as liquid is being drawn into the tube at the distal end.

Figure 1:
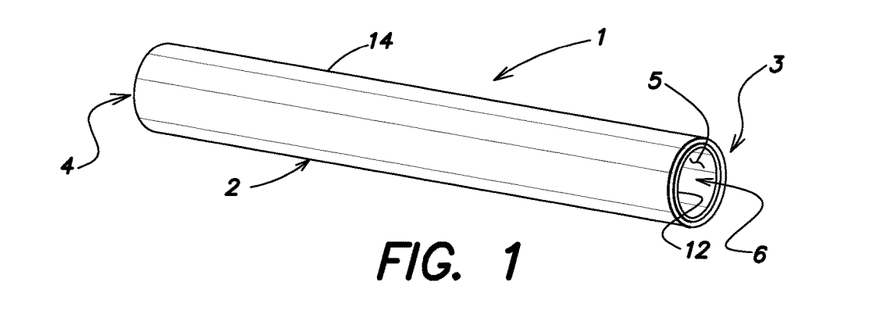
FIG. 1 is a side perspective view of a two layer coextruded capillary tube in accordance with one embodiment of the invention.
Figure 2:
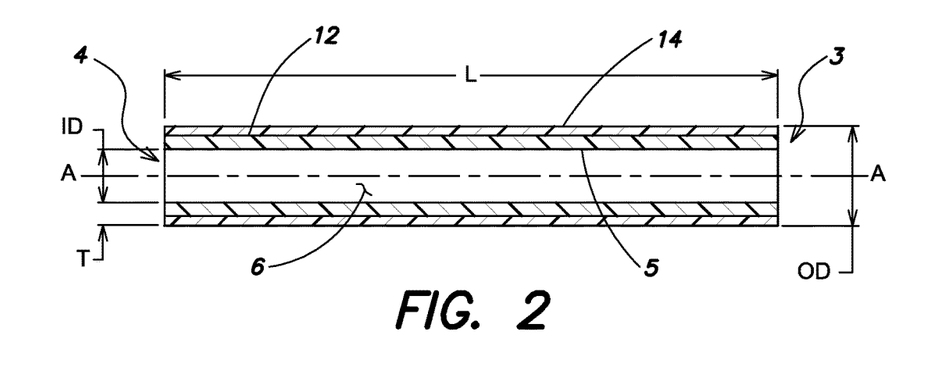
FIG. 2 is a vertical sectional view, taken lengthwise along the longitudinal axis of the tube of FIG. 1.

The tube 1 is a continuous tubular body of multiple coextruded polymer material layers 12, 14 extending coaxially along the entire length L of the tube, as shown in the lengthwise cross sectional view of FIG. 2. Typically the tubular body is substantially cylindrical, extending some length L along an elongated tube axis A, and having a total sidewall of thickness T extending from an inner tube diameter ID to an outer tube diameter OD. The ID is sized, and the innermost layer polymer material is selected, to permit liquid to be drawn into the tubular body by capillary action. The coextruded innermost layer material 12 forms surface 5 of the central bore 6; no coating is required on this surface 5 to provide the desired capillary action. The OD is sized, and the outer one or more layer materials 14 are selected to provide sufficient flexural strength for rigidity and desirable handling characteristics to the tube for the intended application. This is accomplished by utilizing a material in at least one of the one or more outer layer(s) which has a flexural modulus at or greater than about 250,000 psi (pounds per square inch). Typically the multi-layer tube will comprise two layers or three layers, made of different thermoplastic polymer materials that are coextruded in a continuous extrusion process to form an extended length of tubing. Individual capillary tubes may then be cut from the length of tubing at desired lengths. In one example shown in FIGS. 1-3A, the tube has a two material, two layer (2M, 2L) sidewall, including an innermost layer 12 comprising a polyether block polyamide polymer material, and an outermost layer 14 comprising semi-crystalline or amorphous polyester polymer material. This combination provides: a desirable rate of capillary action for aqueous based liquids (e.g., blood); desired handling characteristics (e.g., based on flexural modulus of the material utilized in the outer layer 14 of a two layer tube, and/or the materials of an intermediate layer 23 and outermost layer 24 of a three layer tube 20 as shown in FIG. 3B). The inner layer may be either a polyether block polyamide polymer, or a blend of the polyether block polyamide and a base resin.

Figure 3A:
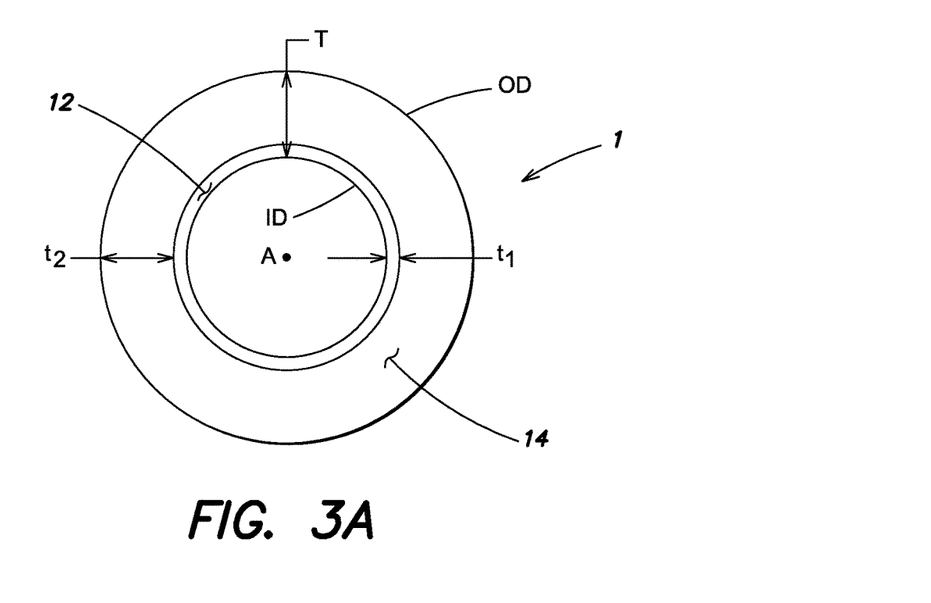
FIG. 3A is a cross sectional view of the multilayer tube of FIG. 1, showing the multiple layers across the tube wall according to one embodiment of the invention.
Figure 3B:
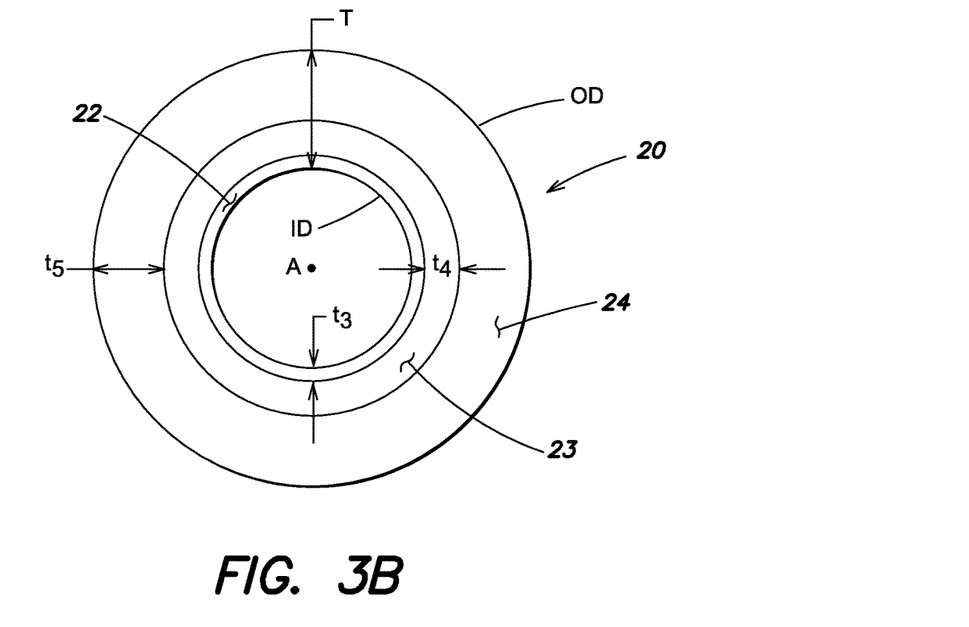
FIG. 3B is a cross sectional view of a multilayer tube having a three layer structure, showing the multiple layers across the tube wall according to another embodiment of the invention.

FIG. 3A illustrates a cross sectional view of a particular two material, two layer (2M2L) capillary tube 1, having an innermost layer 12 of thickness $t_1$ comprising polyether block polyamide polymer material and an outermost layer 14 of thickness $t_2$ comprising an amorphous or semi-crystalline polyester polymer material. In this example the layer thicknesses are: $t_1$=0.002 inches and $t_2$=0.012 inches.

FIG. 3B illustrates a cross sectional view of a particular three material, three layer (3M3L) capillary tube 20, having an innermost layer 22 of thickness $t_3$ comprising polyether block polyamide polymer material, an intermediate layer 23 of thickness $t_4$ comprising an amorphous or semi-crystalline polyester polymer material, and an outermost layer 24 of thickness $t_5$ comprising an amorphous or semi-crystalline polyester material. In the 3M/3L example, the layer thicknesses are: $t_3$=0.002 inches, $t_4$=0.008 inches, and $t_5$=0.012 inches. In both examples (FIGS. 3A and 3B), the tube inner diameter ID may range from 0.010 to 0.1 inches (0.01 to 0.25 cm), and the total tube wall thickness T may range from 0.003 to 0.060 inches. The specific layer thicknesses may vary in different examples depending on the materials used and application. The tube size will also vary based on the application or fluid sample size. In one example the tube sized is for collecting a sample of least about 0.5 microliters. In another example the tube is sized for collecting a sample of from about 0.5 to about 2 microliters. In another example the tube comprises a medical tube sized for collecting blood or other aqueous based fluids.

The polyether block polyamide (PEBA) of the innermost layer 12, 22 is hydrophilic, so as to draw aqueous based solutions into the tube. PEBA is a thermoplastic elastomer, with flexural moduli at or below 75,000 psi as tested by either ISO 178 or ASTM D790, and is made of flexible and hydrophilic polyether (PE), and rigid polyamide (PA). It is a block copolymer obtained by polycondensation of a carboxylic acid polyamide (e.g., polyamide 6 (PA6), polyamide 11 (PA11), or polyamide 12 (PA12)) with a hydroxy terminated polyether (e.g., polytetramethylene glycol (PTMG), or polyethylene glycol (PEG)). The general chemical structure is: HO—(CO—PA-CO—O—PE-O)n-H.

Commercially available PEBA material is known under the trade name of Pebax® (Arkema Specialty Polyamides, Colombes Cedex, France, arkema.com). One suitable PEBA material, sold under the designation Pebax MV1074 by Arkema, has a flexural modulus of approximately 11,600 psi, and is a hydrophilic block copolymer consisting of about 45% of hard polyamide-block (PA12) and about 55% of a soft polyethylene glycol (PEG)-block. See for example the description of Pebax materials in Bondar V. I., Freeman B. D., and Pinnau I., *Gas sorption and characterization of poly(ether-b-amide) segmented block copolymers*, Journal of Polymer Science, Part B: Polymer Physics, 1999, 37(17), p. 2463-2475. Other grades of Pebax may be used as well, such as Pebax MV2080, which has a flexural modulus of approximately 11,600 psi, Pebax 400, which has a flexural modulus of approximately 49,300 psi, or Pebax MH1657, which has a flexural modulus of approximately 11,600 psi.

As described further below, the PEBA can be used either alone or in a blend with a base resin, such as those selected from the group of polyesters, acrylic resins, styrenic resins, acetal resins, polyamides, and polyolefins, such as polyethylene and polypropylene, and copolymers of polyolefins, such as polyethylene vinyl acetates (EVA), and all combinations and blends thereof.

The capillary action exhibited by the innermost tube layer is a function of both the nature of the polymer and the diameter of the tube bore. As commonly understood, capillary action is the ability of a liquid to flow in a narrow space without assistance of, and in opposition to, external forces such as gravity. It occurs when the tube diameter is sufficiently small and when the intermolecular interaction or adhesion of the liquid to the material comprising the inner surface of the tube wall is stronger than the cohesive forces between the liquid molecules.

EXAMPLES

In all the examples below, multi-layer capillary tubes (0.033 inch ID×0.061 inch OD×0.014 inch wall thickness) were manufactured in a co-extrusion process known to those skilled in the art. The respective thicknesses of each layer of a two material, two layer tube (e.g., FIG. 3A), and each layer of a three material, three layer tube (e.g., FIG. 3B), were controlled by the extrusion tooling utilized, such as the "Tri Die" extrusion apparatus manufactured by the Genca Division of General Cable Company, Clearwater, Fla. The extrusion apparatus was selected so as to provide a uniform thickness of the layers along the substantial entirety of the axial length L of all layers in the tube.

The measurement of capillary action, or liquid flow uptake, for the respective tubes was performed in the following manner. A pre-cut tube of length L of 2.950 inches was held at approximately a 30° acute angle and brought into contact with a 1 mL (milliliter) drop of water which was contained in a small aluminum pan. The tube was held in place for a period of 10 seconds while in contact with the drop of water and withdrawn after 10 seconds. The length of travel of the water up into the central bore of the tube, in inches, was then measured with digital dial calipers (Dura-Tool™ model 22-8582) and the results were recorded.

Figure 4:
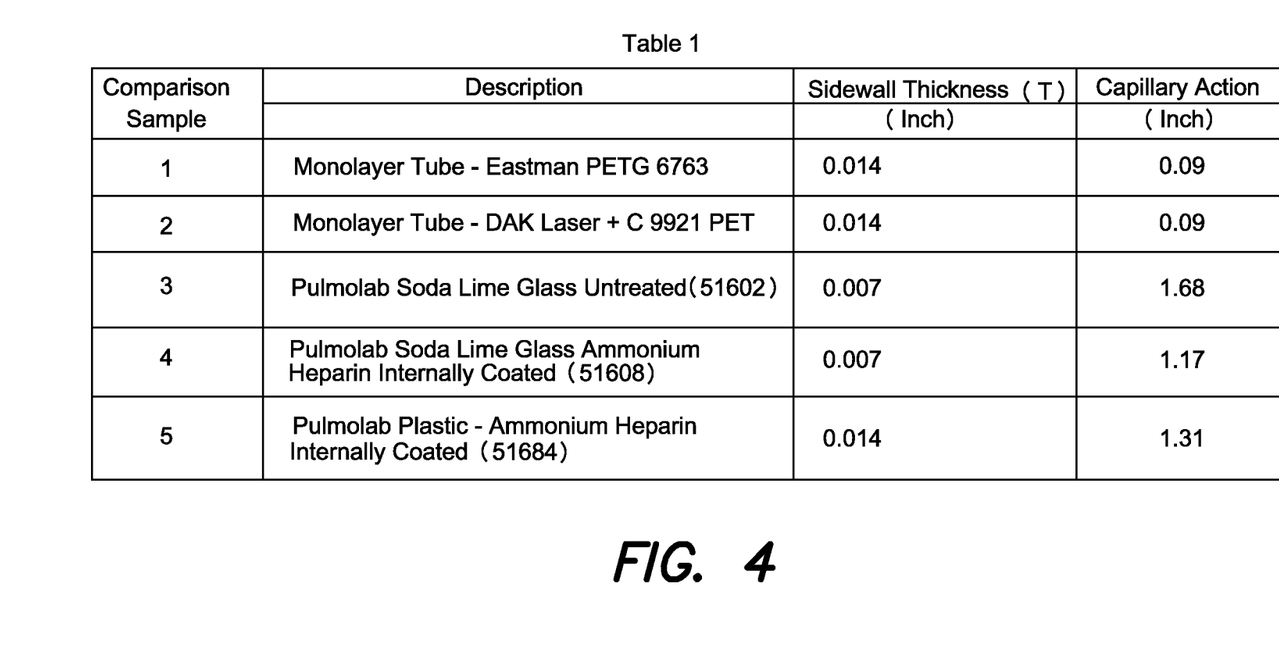
FIG. 4 (Table 1) sets forth values of capillary action for various comparison samples.

FIG. 4 (Table 1) lists as a basis of comparison the measured capillary action of various monolayer tubes made from plastic and glass materials, some of which were pre-treated with an ammonium heparin coating as listed in the description. FIG. 4 (Table 1) also lists the sidewall thickness T of the tubes. In the first two Comparison Samples 1 and 2, monolayer tubes were manufactured via the extrusion process and dimensions described above and were constructed of an amorphous polyester, Eastman 6763 PETG material (Eastman Chemical, Kingsport, Tenn., USA) and a semi-crystalline polyester, DAK Laser +C 9921 PET (DAK Americas, Wilmington, N.C., USA), respectively. The Eastman 6763 PETG material has a flexural modulus of approximately 300,000 psi and the DAK Laser +C 9921 PET has a flexural modulus of approximately 363,000 psi as measured per ASTM D790. The other tube materials listed in FIG. 4 (Table 1) (Comparison Samples 3, 4 and 5), along with their product codes, were purchased from Pulmolab (Porter Ranch, Calif., USA, www.pulmolab.com). The glass tubes (Samples 3 and 4) were described by Pulmolab as made with soda lime glass and were obtained both with and without an ammonium heparin internal coating. The ID of the glass tubes was listed in the range of 0.043 to 0.047 inches. The plastic tube (Sample 5) purchased from Pulmolab was listed to have an ammonium heparin internal coating. The ID of this plastic tube was listed in the range of 0.033 to 0.037 inches.

Figure 5A:
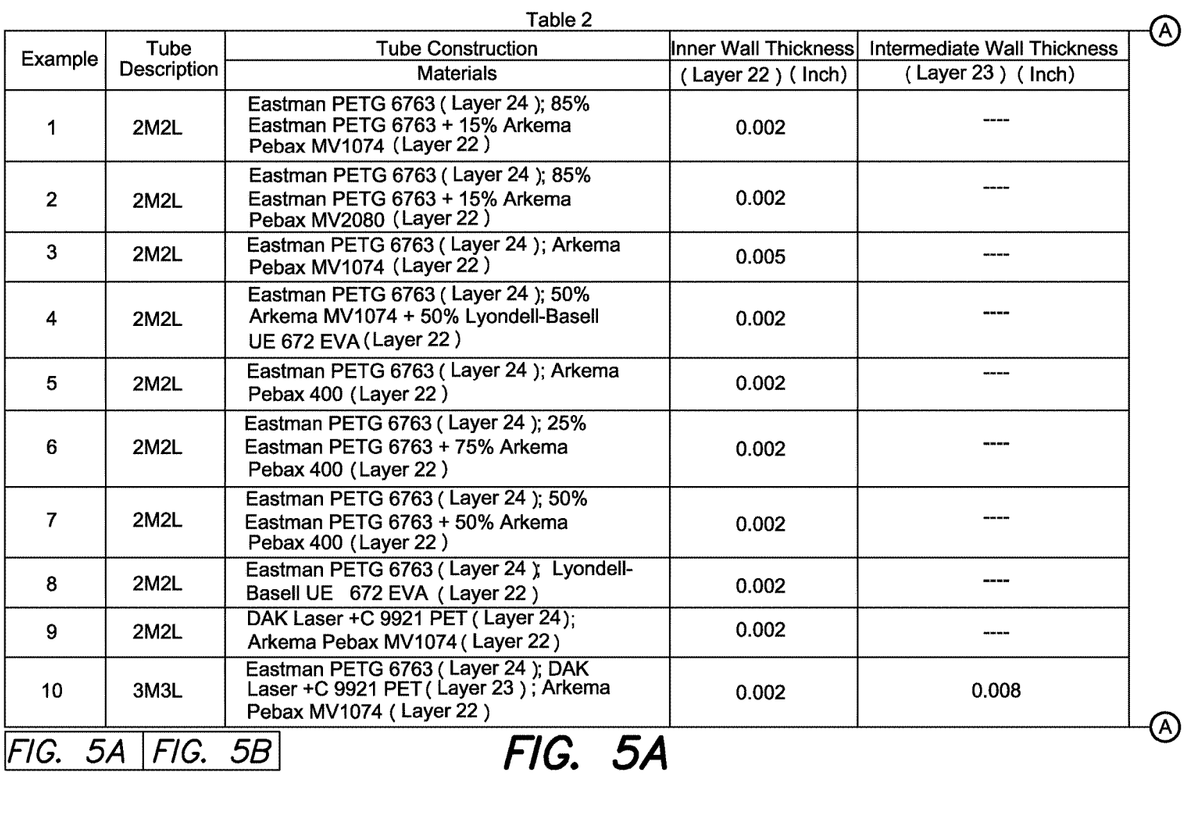
FIGS. 5A and 5B (Table 2) set forth values of capillary action for various embodiments of the invention, FIG. 5A containing columns 1-5 and FIG. 5B containing columns 6-9.
Figure 5B:
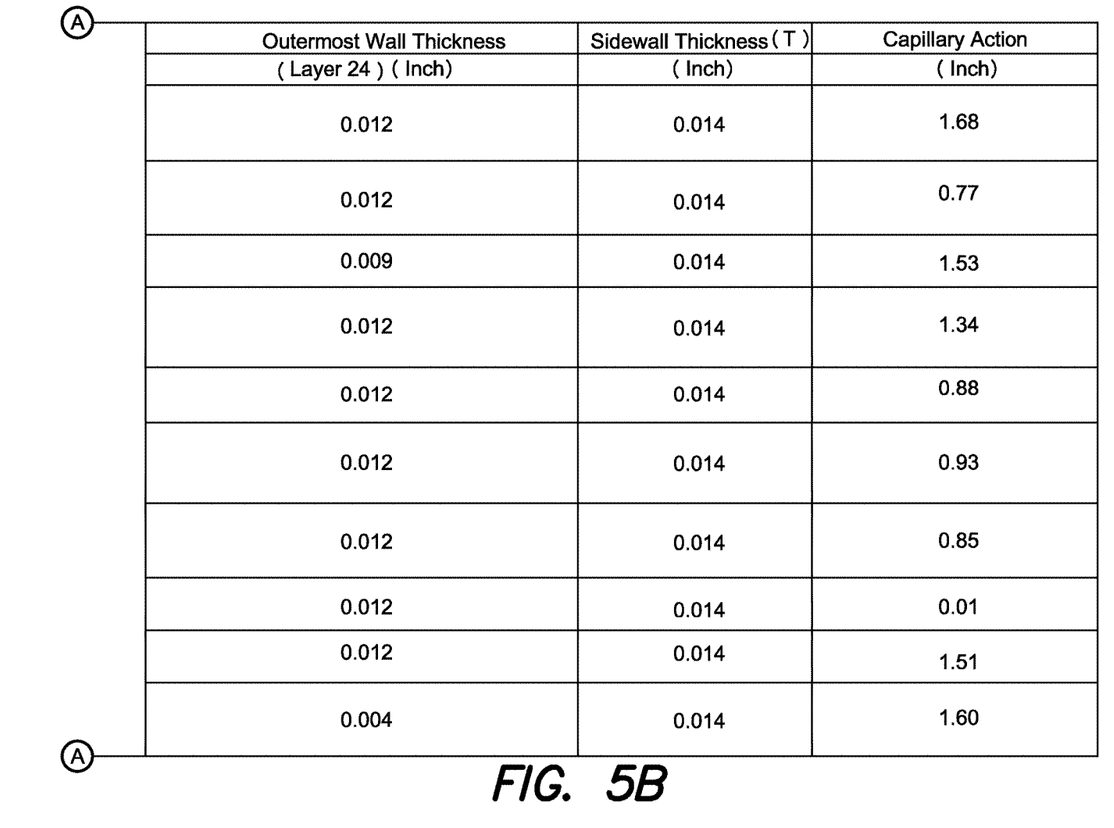

FIGS. 5A and 5B (Table 2) compares the measured capillary action of various two material, two layer (2M2L) (Examples 1-9), and three material three layer (3M3L) (Example 10) capillary tubes manufactured via the extrusion process and dimensions described above. FIGS. 5A and 5B (Table 2) describes the materials and thicknesses thereof utilized in layers 12 and 14 of the 2M2L capillary tube of FIG. 3A, and the materials and thicknesses utilized in layers 22, 23 and 24 of the 3M3L capillary tube of FIG. 3B. FIGS. 5A and 5B (Table 2) also lists the overall sidewall thickness T of the tubes. Examples 1 through 8 are constructed as 2M2L capillary tubes with Eastman 6763 PETG as the outer layer 14. Example 9 utilizes DAK Americas Laser +C 9921 PET as outer layer 14. Example 10 is constructed as a 3M3L capillary tube and utilizes Eastman 6763 PETG as the outer layer 24 and DAK Americas Laser +C 9921 PET as intermediate layer 23. Examples 1, 2, 6 and 7 utilize a blend of PEBA (in weight %) and another base resin as described as inner layer 12. Example 4 utilizes a blend of PEBA (in weight %) with Lyondell-Basell UE672 EVA, a polyethylene vinyl acetate copolymer, as the base resin for inner layer 12 (Lyondell-Basell Industries, Houston, Tex., USA). Examples 3, 5, 9 and 10 utilize only PEBA as inner layer 12, 22. Example 8 is a comparison example and utilizes Lyondell-Basell UE672 EVA (no PEBA polymer) as inner layer 12.

As can be seen from Tables 1 and 2, for plastic capillary tubes which do not have an internal coating and do not comprise PEBA as inner layer 12, the capillary action is minimal and below 0.1 inches of water uptake. This is exemplified by Example 8 of FIGS. 5A and 5B (Table 2) and by Comparison Samples 1 and 2 of FIG. 4 (Table 1). Examples 1-7 and 9-10 of FIGS. 5A and 5B (Table 2), comprising plastic capillary tubes of either the 2M2L (Examples 1-7 and 9) or 3M3L (Example 10) construction, and which comprise PEBA either alone or as a blend with a base resin as the inner layer 12, 22, show much improved capillary action at a minimum of seven (7) times greater water uptake volume as compared to having no PEBA in inner layer 12. Likewise, as compared to glass capillary tubes with or without a pre-treated internal coating as listed in Comparison Samples 3 and 4 of FIG. 4 (Table 1), or with plastic capillary tubes with a pre-treated internal coating as listed in Comparison Sample 5 of FIG. 4 (Table 1), plastic capillary tubes as of either the 2M2L (Examples 1-7 and 9) or 3M3L (Example 10) construction which comprise PEBA either alone or as a blend with a base resin in the inner layer 22, show comparable capillary action.

These and other embodiments of the invention will be apparent to the skilled person and the invention is not limited to the foregoing examples.

The invention claimed is:

1. A capillary tube comprising:
   a coextruded plastic multilayer capillary tube having a tubular sidewall defining a central channel and comprising at least two coextruded polymer layers coaxially disposed along an axial length of the tube between open proximal and distal ends of the tube, the tubular sidewall having an inner diameter sized to permit an aqueous or aqueous based fluid to flow into the central channel by capillary action through an open end of the tube,
   the at least two coaxial coextruded polymer layers comprising:
   an innermost layer defining the surface of the central channel comprising a polyether block polyamide (PEBA) polymer material; and
   an outer layer of a material having a flexural modulus of at least about 250,000 pounds per square inch (psi).

2. The capillary tube of claim 1 wherein the material comprising the innermost layer has a flexural modulus of at least about 11,000 psi.

3. The capillary tube of claim 1 wherein:
   the innermost layer material comprises a blend of PEBA and a base resin.

4. The capillary tube of claim 3 wherein:
   the base resin is selected from the group consisting of polyesters, acrylic resins, styrenic resins, acetal resins, polyamides, polyolefins and polyolefin copolymers, and all combinations and blends thereof.

5. The capillary tube of claim 1 wherein
   the central channel has a diameter in a range of from about 0.01 inches to about 0.10 inches;
   the tubular sidewall has a thickness in a range of form about 0.003 inches to about 0.060 inches; and
   the innermost layer has a thickness in a range of from about 0.001 inches to about 0.059 inches.

6. The capillary tube of claim 1 wherein:
   the tubular sidewall has two layers, including the outer layer of semi-crystalline or amorphous polyester polymer material, and the innermost layer comprising PEBA or a blend of PEBA and a base resin.

7. The capillary tube of claim 6 wherein:
   the central channel has a diameter in a range of from about 0.01 inches to about 0.10 inches;
   the tubular sidewall has a thickness in a range of from about 0.003 inches to about 0.060 inches; and
   the innermost layer has a thickness in a range of from about 0.001 inches to about 0.059 inches.

8. The capillary tube of claim 1 wherein:
   the tubular sidewall has three layers, the outer layer being an outermost layer comprising semi-crystalline or amorphous polyester polymer material, an intermediate layer comprising semi-crystalline or amorphous polyester polymer material, and the innermost layer comprising PEBA or a blend of PEBA and a base resin.

9. The capillary tube of claim 8 wherein:
   the outermost layer has a thickness in a range of from about 0.0005 inches to about 0.058 inches, the intermediate layer has a thickness in a range of from about 0.0005 inches to about 0.058 inches, the innermost layer has a thickness in a range of from about 0.001 inches to about 0.059 inches, and the central channel has a diameter in a range of from about 0.01 inches to about 0.100 inches.

10. The capillary tube of claim 1 wherein the sidewall outer layer is an outermost layer of semi-crystalline polyester polymer material.

11. The capillary tube of claim 1 wherein the capillary tube comprises a medical tube for collecting a sample of blood or other aqueous based fluid.

12. A medical device for collecting a sample of blood or other aqueous based fluid including the capillary tube of claim 1.

13. A method of collecting a fluid sample comprising inserting an open end of the capillary tube of claim 1 into a fluid specimen and drawing fluid from the specimen into the channel via capillary action.

14. The capillary tube of claim 1, wherein the capillary tube is sized for collecting a sample of at least 0.5 microliters.

15. The capillary tube of claim 1, wherein the capillary tube is sized for collecting a sample from about 0.5 to about 2 microliters.

16. A method of making a coextruded plastic multilayer capillary tube comprising:
    coextruding a tubular sidewall of a coextruded plastic multilayer capillary tube, the tubular sidewall comprising at least two coextruded polymer layers coaxially disposed along an axial length of the tube between open proximal and distal ends of the tube, the tubular sidewall defining a central channel for receiving a fluid,
    the tubular sidewall having an inner diameter sized to permit an aqueous or aqueous based fluid to flow into the central channel by capillary action through an open end of the tube,
    the at least two coaxial coextruded polymer layers comprising: an innermost layer defining the surface of the central channel comprising a polyether block polyamide (PEBA) polymer material, and an outermost layer of a material having a flexural modulus of at least about 250,000 pounds per square inch (psi).

17. A capillary tube comprising:
    a coextruded plastic multilayer capillary tube having a tubular sidewall defining a central channel and comprising three coextruded polymer layers coaxially disposed along an axial length of the tube between open proximal and distal ends of the tube, the tubular sidewall having an inner diameter sized to permit an aqueous or aqueous based fluid to flow into the central channel by capillary action through an open end of the tube, the three coaxial coextruded polymer layers comprising:
    an innermost layer defining the surface of the central channel comprising a polyether block polyamide (PEBA) or a blend of PEBA and a base resin polymer material;
    an intermediate layer comprising semi-crystalline or amorphous polyester polymer material; and
    an outermost layer comprising semi-crystalline or amorphous polyester polymer material having a flexural modulus of at least about 250,000 pounds per square inch (psi).

18. The capillary tube of claim 17 wherein:
    the outermost layer has a thickness in a range of from about 0.0005 inches to about 0.058 inches, the intermediate layer has a thickness in a range of from about 0.0005 inches to about 0.058 inches, the innermost layer has a thickness in a range of from about 0.001 inches to about 0.059 inches, and the central channel has a diameter in a range of from about 0.01 inches to about 0.100 inches.

19. The capillary tube of claim 17, wherein the material comprising the innermost layer has a flexural modulus of at least about 11,000 psi.

20. The capillary tube of claim 17 wherein:
the innermost layer material comprises the blend of PEBA and base resin polymer material.

21. The capillary tube of claim 17 wherein:
the base resin polymer material is selected from the group consisting of polyesters, acrylic resins, styrenic resins, acetal resins, polyamides, polyolefins and polyolefin copolymers, and all combinations and blends thereof.

22. The capillary tube of claim 17 wherein
the central channel has a diameter in a range of from about 0.01 inches to about 0.10 inches;
the tubular sidewall has a thickness in a range of form about 0.003 inches to about 0.060 inches; and
the innermost layer has a thickness in a range of from about 0.001 inches to about 0.059 inches.

23. The capillary tube of claim 17 wherein the outermost layer is semi-crystalline polyester polymer material.

24. The capillary tube of claim 17 wherein the capillary tube comprises a medical tube for collecting a sample of blood or other aqueous based fluid.

25. A medical device for collecting a sample of blood or other aqueous based fluid including the capillary tube of claim 17.

26. A method of collecting a fluid sample comprising inserting an open end of the capillary tube of claim 17 into a fluid specimen and drawing fluid from the specimen into the channel via capillary action.

27. The capillary tube of claim 17, wherein the capillary tube is sized for collecting a sample of at least 0.5 microliters.

28. The capillary tube of claim 17, wherein the capillary tube is sized for collecting a sample from about 0.5 to about 2 microliters.

* * * * *

UNITED STATES PATENT AND TRADEMARK OFFICE
CERTIFICATE OF CORRECTION

PATENT NO.         : 9,681,833 B2  
APPLICATION NO.    : 14/256342  
DATED              : June 20, 2017  
INVENTOR(S)        : Olasavsky et al.

Page 1 of 1

It is certified that error appears in the above-identified patent and that said Letters Patent is hereby corrected as shown below:

In the Claims

In Column 7, Line 33 (Claim 5) delete "form" and insert --from--

Signed and Sealed this  
First Day of August, 2017

Joseph Matal  
*Performing the Functions and Duties of the*  
*Under Secretary of Commerce for Intellectual Property and*  
*Director of the United States Patent and Trademark Office*